(12) United States Patent
Fossa

(10) Patent No.: US 6,265,429 B1
(45) Date of Patent: Jul. 24, 2001

(54) METHOD FOR TREATING CONGESTIVE HEART FAILURE

(75) Inventor: Anthony A. Fossa, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/421,149

(22) Filed: Oct. 19, 1999

Related U.S. Application Data

(60) Provisional application No. 60/105,108, filed on Oct. 21, 1998.

(51) Int. Cl.$^7$ .................................................. A61K 31/415
(52) U.S. Cl. ........................... 514/403; 514/406; 514/407
(58) Field of Search ................................... 514/403, 406, 514/407

(56) References Cited

FOREIGN PATENT DOCUMENTS

WO9742174   11/1997  (WO).

OTHER PUBLICATIONS

Doyama, K. et al., *International Journal of Cardiology*, 54, 1996, pp. 217–225.
Feldman, M.D. et al., *Circulation*, 75, 1987, pp. 331–339.
*The Merck Index*, 12$^{th}$ ed., Merck & Co., Inc., 1996, pp. 456, 1060 and 1672–1673.
Packer, M. et al., *New England Journal of Medicine*, 325(21), 1991, pp. 1468–1475.
Verghese, M.W. et al., *Journal of Molecular & Cellular Cardiology*, 12 (Supp. II), 181, 1989, p. S61.

Primary Examiner—Theodore J. Criares
(74) Attorney, Agent, or Firm—Peter C. Richardson; Gregg C. Benson; Jennifer A. Kispert

(57) ABSTRACT

The present invention relates to methods for treating congestive heart failure in a mammal by administering a congestive heart failure treating amount of a compound which inhibits phosphodiesterase type IV and the production of tumor necrosis factor, such as, for example, a substituted indazol derivative, e.g., of the formula

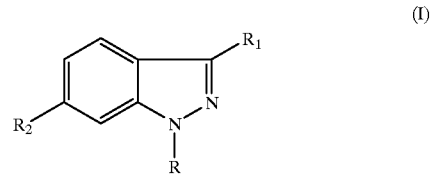

(I)

or a pharmaceutically acceptable salt thereof, wherein R, $R_1$ and $R_2$ are as defined herein. The invention further relates to pharmaceutical compositions for the treatment of congestive heart failure comprising a congestive heart failure treating amount of a compound which inhibits phosphodiesterase type IV and the production of tumor necrosis factor, such as, for example, a substituted indazol derivative, e.g., of formula (I) herein, or a pharmaceutically acceptable salt thereof, and a pharmaceutically acceptable vehicle, diluent or carrier.

11 Claims, No Drawings

METHOD FOR TREATING CONGESTIVE HEART FAILURE

CROSS-REFERENCE TO RELATED APPLICATION

This application claims priority from U.S. Provisional Patent Application No. 60/105,108 filed Oct. 21, 1998, the benefit of which is hereby claimed under 37 C.F.R. §1.78 (a)(3).

FIELD OF THE INVENTION

The present invention relates to novel methods for treating congestive heart failure ("CHF") in mammals, especially humans, with a compound which inhibits phosphodiesterase ("PDE") type IV and the production of tumor necrosis factor ("TNF") and particularly, to such methods wherein said compound is a substituted indazole derivative.

The present invention also relates to pharmaceutical compositions for the treatment of CHF comprising a compound which inhibits PDE type IV and the production of TNF and particularly, to such pharmaceutical compositions wherein said compound is a substituted indazole derivative.

BACKGROUND OF THE INVENTION

As described, for example, by M. Packer et al., in the article "Effect of Oral Milrinone on Mortality in Severe Chronic Heart Failure," published in the *New England Journal of Medicine* 325(21): pp. 1468–1475 (1991), it is well known that patients with CHF generally have impaired cardiac contractility. Milrinone, or 1,6-dihydro-2-methyl-6-oxo-(3,4'-bi-pyridine)-5-carbonitrile, is a known selective PDE inhibitor with vasodilating and positive inotropic activity (see, e.g., *The Merck Index,* 12th ed., Merck & Co., Inc., p. 1060 (1996)) and enhances cardiac contractility see, e.g., M. Packer et al. referenced-above).

Packer et al. also disclosed in the article referenced-above that Milrinone enhances cardiac contractility by increasing intracellular levels of the know "second messenger" (responds to hormones which are considered the "first messengers") cyclic adenosine 3',5'-monophosphate ("cAMP").

As would be understood by those of skill in the relevant art, intracellular levels of CAMP may be increased by either increasing the synthesis of cAMP or decreasing its deactivation or degradation. As described in, e.g., *The Merck Index* referenced-above at page 456, cAMP is produced from adenosine triphosphate ("ATP") by adenylate cyclase and deactivated or degraded by cyclic nucleotide PDEs which convert cAMP to 5'-adenylic acid. Beta-adrenergic agonists provide an increase in cAMP levels while PDEs provide a decrease in cAMP levels.

M. D. Feldman et al., in an article published in *Circulation* 75: pp. 331–9 (1987), reported pharmacological data which showed that deficient production of cAMP in patients with end-stage heart failure caused contractile dysfunction. However, as cautioned by Packer et al. in the article referenced-above, some positive inotropic agents, e.g., certain beta-adrenergic agonists and phosphodiesterase inhibitors, which increase the intracellular concentration of cAMP have been shown to increase mortality in patients with chronic heart failure.

It is accepted by those of skill in the art that distinct classes of PDEs exist. Consequently, selective inhibition of these distinct PDEs has led to improved drug therapy. For example, as described by M. W. Verghese et al., in an article published in the *Journal of Molecular & Cellular Cardiology* 12 (Suppl. II): S61 (1989) and by S. R. O'Donnell et al., in an article published in 37 *Birkhauser-Vedag* (1988), inhibition of PDE Type IV inhibits the release of inflammatory mediators and relaxes airway smooth muscle, respectively. Hence, as would be appreciated by those of skill, compounds that inhibit PDE Type IV, but have poor activity against other PDE types, inhibit the release of inflammatory mediators and relax airway smooth muscle without causing undesirable cardiovascular or anti-platelet effects generally associated with the inhibition of non-Type IV PDEs.

As is well known, for example, as described in *The Merck Index* referenced-above at pages 1672–1673, TNF is a pluripotent cytokine which is produced by, e.g., activated macrophages and human vascular smooth muscle cells, as part of the cellular immune response. As appreciated by those of skill in the relevant art, TNF, or cachetin, is involved in many infectious and auto-immune diseases, and is the central mediator of the inflammatory response seen in sepsis and septic shock.

Further, as is also known, as described by K. Doyama et al., in an article published in the *International Journal of Cardiology* 54: pp. 217–225 (1996), elevated circulating levels of TNF have been reported in patients with various diseases such as, for example, cancer, infectious and inflammatory disorders, and various cardiac diseases, e.g., acute myocardial infarction, myocarditis, and CHF secondary to dilated cardiomyopathy or ischemic heart disease. Moreover, Doyoma et al. also describes in the article referenced-above that TNF depresses cardiac contractility.

The present invention relates to novel methods and pharmaceutical compositions for treating CHF in mammals, especially humans, with or which comprise, respectively, a compound which inhibits PDE type IV and the production of TNF, such as, for example, a substituted indazole derivative.

SUMMARY OF THE INVENTION

The present invention relates to methods for treating CHF in a mammal which comprise administering to the mammal a CHF treating amount of a compound, or a pharmaceutically acceptable salt thereof, which inhibits PDE type IV and the production of TNF.

More particularly, compounds suitable for use in the novel methods for treating CHF according to the present invention include substituted indazole derivatives which are disclosed in commonly-assigned PCT published application WO 97/42174 designating inter alia, the United States, which is incorporated by reference herein in its entirety, including, for example, the compounds of formula (I) below:

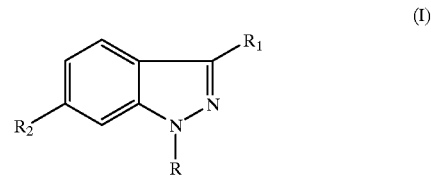

(I)

and the pharmaceutically acceptable salts thereof, wherein:
R is hydrogen, $C_1$–$C_6$ alkyl, —$(CH_2)_n(C_3$–$C_7$ cycloalkyl) wherein n is 0 to 2, $(C_1$–$C_6$ alkoxy)$C_1$–$C_6$ alkyl, $C_2$–$C_6$ alkenyl, —$(CH_2)_n(C_3$–$C_6$ heterocyclyl) wherein n is 0 to 2, or —$(Z')_b(Z'')_c(C_6$–$C_{10}$ aryl) wherein b and c are independently 0 or 1, Z' is $C_1$–$C_6$ alkylene or $C_2$–$C_6$ alkenylene, and Z" is O, S, $SO_2$, or $NR_9$, and wherein said alkyl, alkenyl, alkoxyalkyl, heterocyclyl, and aryl moieties of said R groups are optionally substituted by 1 to 3 substituents independently selected from halo, hydroxy, $C_1$–$C_5$ alkyl, $C_2$–$C_5$ alkenyl, $C_1$–$C_5$ alkoxy, $C_3$–$C_6$ cycloalkoxy, trifluoromethyl, nitro, $CO_2R_9$, $C(O)NR_9R_{10}$, $NR_9R_{10}$ and $SO_2NR_9R_{10}$;

$R_1$ is hydrogen, $C_1$–$C_7$ alkyl, $C_2$–$C_3$ alkenyl, phenyl, $C_3$–$C_7$ cycloalkyl, or ($C_3$–$C_7$ cycloalkyl)$C_1$–$C_2$ alkyl, wherein said alkyl, alkenyl and phenyl $R_1$ groups are optionally substituted by 1 to 3 substituents independently selected from the group consisting of methyl, ethyl, trifluoromethyl, and halo;

$R_2$ is selected from the group consisting of

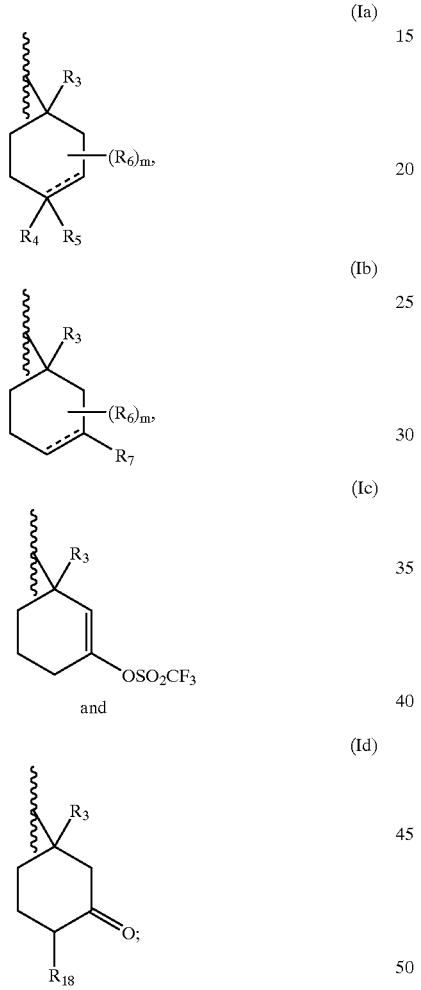

wherein the dashed line in formulae (Ia) and (Ib) represents a single or a double bond;

m is 0 to 4;

$R_3$ is hydrogen, halo, cyano, $C_1$–$C_4$ alkyl optionally substituted by 1 to 3 halo groups, $CH_2NHC(O)C(O)NH_2$, cyclopropyl optionally substituted by $R_{11}$, $R_{17}$, $CH_2OR_9$, $NR_9R_{10}$, $CH_2NR_9R_{10}$, $CO_2R_9$, $C(O)NR_9R_{10}$, $C\equiv CR_{11}$, $C(Z)H$ or $CH=CR_{11}R_{11}$;

$R_4$ is hydrogen, $C(Y)R_{14}$, $CO_2R_{14}$, $C(Y)NR_{17}R_{14}$, CN, $C(NR_{17})NR_{17}R_{14}$, $C(NOR_9)R_{14}$, $C(O)NR_9NR_9C(O)R_9$, $C(O)NR_9NR_{17}R_{14}$, $C(NOR_{14})R_9$, $C(NR_9)NR_{17}R_{14}$, $C(NR_{14})NR_9R_{10}$, $C(NCN)NR_{17}R_{14}$, $C(NCN)S(C_1$–$C_4$ alkyl), $CR_9R_{10}OR_{14}$, $CR_9R_{10}SR_{14}$, $CR_9R_{10}S(O)_nR_{15}$ wherein n is 0 to 2, $CR_9R_{10}NR_{14}R_{17}$, $CR_9R_{10}NR_{17}SO_2R_{15}$, $CR_9R_{10}NR_{17}C(Y)R_{14}$, $CR_9R_{10}NR_{17}CO_2R_{15}$, $CR_9R_{10}NR_{17}C(Y)NR_{17}R_{14}$, $CR_9R_{10}NR_{17}C(NCN)NR_{17}R_{14}$, $CR_9R_{10}NR_{17}C(CR_9NO_2)S(C_1$–$C_4$ alkyl), $CR_9R_{10}CO_2R_{15}$, $CR_9R_{10}C(Y)NR_{17}R_{14}$, $CR_9R_{10}C(NR_{17})NR_{17}R_{14}$, $CR_9R_{10}CN$, $CR_9R_{10}C(NOR_{10})R_{14}$, $CR_9R_{10}C(NOR_{14})R_{10}$, $CR_9R_{10}NR_{17}C(NR_{17})S(C_1$–$C_4$ alkyl), $CR_9R_{10}NR_{17}C(NR_{17})NR_{17}R_{14}$, $CR_9R_{10}NR_{17}C(O)C(O)NR_{17}R_{14}$, $CR_9R_{10}NR_{17}C(O)C(O)OR_{14}$, tetrazolyl, thiazolyl, imidazolyl, imidazolidinyl, pyrazolyl, thiazolidinyl, oxazolyl, oxazolidinyl, triazolyl, isoxazolyl, oxadiazolyl, thiadiazolyl, $CR_9R_{10}$(tetrazolyl), $CR_9R_{10}$(thiazolyl), $CR_9R_{10}$(imidazolyl), $CR_9R_{10}$(imidazolidinyl), $CR_9R_{10}$(pyrazolyl), $CR_9R_{10}$(thiazolidinyl), $CR_9R_{10}$(oxazolyl), $CR_9NR_{10}$(oxazolidinyl), $CR_9R_{10}$(triazolyl), $CR_9NR_{10}$(isoxazolyl), $CR_9R_{10}$(oxadiazolyl), $CR_9R_{10}$(thiadiazolyl), $CR_9R_{10}$(morpholinyl), $CR_9R_{10}$(piperidinyl), $CR_9R_{10}$(piperazinyl), or $CR_9R_{10}$(pyrrolyl), wherein said heterocyclic groups and moieties for said $R_4$ substituents are optionally substituted by 1 to 3 $R_{14}$ substituents;

$R_5$ is $R_9$, $OR_9$, $CH_2OR_9$, cyano, $C(O)R_9$, $CO_2R_9$, $C(O)NR_9R_{10}$, or $NR_9R_{10}$, provided that $R_5$ is absent when the dashed line in formula (Ia) represents a double bond;

or $R_4$ and $R_5$ are taken together to form =O, or $R_8$;

or $R_5$ is hydrogen and $R_4$ is $OR_{14}$, $SR_{14}$, $S(O)_nR_{15}$ wherein n is 0 or 2, $SO_2NR_{17}R_{14}$, $NR_{17}R_{14}$, $NR_{14}C(O)R_9$, $NR_{17}C(Y)R_{14}$, $NR_{17}C(O)OR_{15}$, $NR_{17}C(Y)NR_{17}R_{14}$, $NR_{17}SO_2NR_{17}R_{14}$, $NR_{17}C(NCN)NR_{17}R_{14}$, $NR_{17}SO_2R_{15}$, $NR_{17}C(CR_9,NO_2)NR_{17}R_{14}$, $NR_{17}C(NCN)S(C_1$–$C_4$ alkyl), $NR_{17}C(CR_9NO_2)S(C_1$–$C_4$ alkyl), $NR_{17}C(NR_{17})NR_{17}R_{14}$, $NR_{17}C(O)C(O)NR_{17}R_{14}$, or $NR_{17}C(O)C(O)OR_{14}$;

each $R_6$ is independently selected from methyl and ethyl optionally substituted by 1 to 3 halo groups;

$R_7$ is $OR_{14}$, $SR_{14}$, $SO_2NR_{17}R_{14}$, $NR_{17}R_{14}$, $NR_{14}C(O)R_9$, $NR_{17}C(Y)R_{14}$, $NR_{17}C(O)OR_{15}$, $S(O)_nR_{12}$ wherein n is 0 to 2, $OS(O)_2R_{12}$, $OR_{12}$, $OC(O)NR_{13}R_{12}$, $OC(O)R_{13}$, $OCO_2R_{13}$, $O(CR_{12}R_{13})_mOR_{12}$ wherein m is 0 to 2, $CR_9R_{10}OR_{14}$, $CR_9R_{10}NR_{17}R_{14}$, $C(Y)R_{14}$, $CO_2R_{14}$, $C(Y)NR_{17}R_{14}$, CN, $C(NR_{17})NR_{17}R_{14}$, $C(NOR_9)R_{14}$, $C(O)NR_9NR_9C(O)R_9$, $C(O)NR_9NR_{17}R_{14}$, $C(NOR_{14})R_9$, $C(NR_9)NR_{17}R_{14}$, $C(NR_{14})NR_9R_{10}$, $C(NCN)NR_{17}R_{14}$, $C(NCN)S(C_1$–$C_4$ alkyl), tetrazolyl, thiazolyl, imidazolyl, imidazolidinyl, pyrazolyl, thiazolidinyl, oxazolyl, oxazolidinyl, triazolyl, isoxazolyl, oxadiazolyl, or thiadiazolyl, wherein said $R_7$ heterocyclic groups are optionally substituted by 1 to 3 $R_{14}$ substituents;

$R_8$ is $=NR_{15}$, $=NCR_9R_{10}(C_2$–$C_6$ alkenyl), $=NOR_{14}$, $=NOR_{19}$, $=NOCR_9R_{10}(C_2$–$C_6$ alkenyl), $=NNR_9R_{14}$, $=NNR_9R_{19}$, $=NCN$, $=NNR_9C(Y)NR_9R_{14}$, $=C(CN)_2$, $=CR_{14}CN$, $=CR_{14}CO_2R_9$, $=CR_{14}C(O)NR_9R_{14}$, $=C(CN)NO_2$, $=C(CN)CO_2(C_1$–$C_4$ alkyl), $=C(CN)OCO_2(C_1$–$C_4$ alkyl), $=C(CN)(C_1$–$C_4$ alkyl), $=C(CN)C(O)NR_9R_{14}$, 2-(1,3-dithiane), 2-(1,3-dithiolane), dimethylthio ketal, diethylthio ketal, 2-(1,3-dioxolane), 2-(1,3-dioxane), 2-(1,3-oxathiolane), dimethyl ketal or diethyl ketal;

each $R_9$ and $R_{10}$ is independently hydrogen or $C_1$–$C_4$ alkyl optionally substituted by up to three fluorine atoms;

each $R_{11}$ is independently fluoro or $R_{10}$;

each $R_{12}$ is independently $C_1$–$C_6$ alkyl, $C_2$–$C_3$ alkenyl, $C_3$–$C_7$ cycloalkyl, ($C_3$–$C_7$ cycloalkyl)$C_1$–$C_2$ alkyl, $C_6$–$C_{10}$ aryl, or $C_3$–$C_9$ heterocyclyl, wherein said $R_{12}$ groups are optionally substituted by 1 to 3 substituents independently selected from the group consisting of methyl, ethyl, trifluoromethyl, and halo;

each $R_{13}$ is independently hydrogen or $R_{12}$;

each $R_{14}$ is independently hydrogen or $R_{15}$, or when $R_{14}$ and $R_{17}$ are as $NR_{17}R_{14}$ then $R_{17}$ and $R_{14}$ can be taken together with the nitrogen to form a 5 to 7 membered ring optionally containing at least one additional heteroatom selected from O, N and S;

each $R_{15}$ is independently $C_1$–$C_6$ alkyl or —$(CR_9R_{10})_nR_{16}$ wherein n is 0 to 2 and $R_{16}$ and said $C_1$–$C_6$ alkyl are optionally substituted by 1 to 3 substituents independently selected from halo, nitro, cyano, $NR_{10}R_{17}$, $C(O)R_9$, $OR_9$, $C(O)NR_{10}OR_{17}$, $OC(O)NR_{10}R_{17}$, $NR_{17}C(O)NR_{17}R_{10}$, $NR_{17}C(O)R_{10}$, $NR_{17}C(O)O(C_1$–$C_4$ alkyl), $C(NR_{17})NR_{17}R_{10}$, $C(NCN)NR_{17}R_{10}$, $C(NCN)S(C_1$–$C_4$ alkyl), $NR_{17}C(NCN)S(C_1$–$C_4$ alkyl), $NR_{17}C(NCN)NR_{17}R_{10}$, $NR_{17}SO_2(C_1$–$C_4$ alkyl), $S(O)_n(C_1$–$C_4$ alkyl) wherein n is 0 to 2, $NR_{17}C(O)C(O)NR_{17}R_{10}$, $NR_{17}C(O)C(O)R_{17}$, thiazolyl, imidazolyl, oxazolyl, pyrazolyl, triazolyl, tetrazolyl, and $C_1$–$C_2$ alkyl optionally substituted with one to three fluorine atoms;

each $R_{16}$ is independently $C_3$–$C_7$ cycloalkyl, pyridyl, pyrimidyl, pyrazolyl, imidazolyl, triazolyl, pyrrolyl, piperazinyl, piperidinyl, morpholinyl, furanyl, thienyl, thiazolyl, quinolinyl, naphthyl, or phenyl;

each $R_{17}$ is independently $OR_9$ or $R_{10}$;

$R_{18}$ is H, $C(Y)R_{14}$, $CO_2R_{14}$, $C(Y)NR_{17}R_{14}$, CN, $C(NR_{17})NR_{17}R_{14}$, $C(NOR9)R_{14}$, $C(O)NR_9NR_9C(O)R_9$, $C(O)NR_9NR_{17}R_{14}$, $C(NOR_{14})R_9$, $C(NR_9)NR_{17}R_{14}$, $C(NR_{14})NR_9R_{10}$, $C(NCN)NR_{17}R_{14}$, $C(NCN)S(C_1$–$C_4$ alkyl), $CR_9NR_{10}OR_{14}$, $CR_9R_{10}SR_{14}$, $CR_9R_{10}S(O)_nR_{15}$ wherein n is 0 to 2, $CR_9R_{10}NR_{14}R_{17}$, $CR_9R_{10}NR_{17}SO_2R_{15}$, $CR_9R_{10}NR_{17}C(Y)R_{14}$, $CR_9R_{10}NR_{17}CO_2R_{15}$, $CR_9R_{10}NR_{17}C(Y)NR_{17}R_{14}$, $CR_9R_{10}NR_{17}C(NCN)NR_{17}R_{14}$, $CR_9R_{10}NR_{17}C(CR_9NO_2)S(C_1$–$C_4$ alkyl), tetrazolyl, thiazolyl, imidazolyl, imidazolidinyl, pyrazolyl, thiazolidinyl, oxazolyl, oxazolidinyl, triazolyl, isoxazolyl, oxadiazolyl, thiadiazolyl, wherein said heterocyclic groups are optionally substituted by 1 to 3 $R_{14}$ substituents;

$R_{19}$ is —$C(O)R_{14}$, —$C(O)NR_9R_{14}$, —$S(O)_2R_{15}$, or —$S(O)_2NR_9R_{14}$;

each Y is independently =O or =S; and

Z is =O, =$NR_{17}$, =NCN, =$C(CN)_2$, =$CR_9CN$, =$CR_9NO_2$, =$CR_9CO_2R_9$, =$CR_9C(O)NR_9R_{10}$; =$C(CN)CO_2(C_{1-4}$ alkyl) or =$C(CN)C(O)NFR_9R_{10}$.

The term "halo," as used herein, unless otherwise indicated, means fluoro, chloro, bromo or iodo. Preferred halo groups are fluoro, chloro and bromo.

The term "alkyl," as used herein, unless otherwise indicated, includes saturated monovalent hydrocarbon radicals having straight or branched moieties.

The term "alkoxy," as used herein, unless otherwise indicated, includes O-alkyl groups wherein "alkyl" is defined above.

The term "alkenyl," as used herein, unless otherwise indicated, includes unsaturated alkyl groups having one or more double bonds wherein "alkyl" is as defined above.

The term "cycloalkyl," as used herein, unless otherwise indicated, includes saturated monovalent cyclo hydrocarbon radicals including cyclobutyl, cyclopentyl and cycloheptyl.

The term "heterocyclyl," as used herein, unless otherwise indicated, includes aromatic and non-aromatic heterocyclic groups containing one or more heteroatoms each selected from O, S and N. The heterocyclic groups include benzo-fused ring systems and ring systems substituted with an oxo moiety. With reference to the $R_4$ substituent of formula (Ia), the $C_3$–$C_9$ heterocyclic group can be attached to the $C_1$–$C_6$ alkyl group by a nitrogen or, preferably, a carbon atom. An example of a $C_3$ heterocyclic group is thiazolyl, and an example of a $C_9$ heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

Where heterocyclic groups are specifically recited or covered as substituents for the compound of formula (I), it is understood that all suitable isomers of such heterocyclic groups are intended. Thus, for example, in the definition of the substituent $R_4$, the term "thiazolyl" includes 2-, 4- or 5-thiazolyl; the term "imidazolyl" includes 2-, 4- or 5-imidazolyl; the term "pyrazolyl" includes 3-, 4- or 5-pyrazolyl; the term "oxazolyl" includes 2-, 4- or 5-oxazolyl; the term "isoxazolyl" includes 3-, 4- or 5-isoxazolyl, and so on. Likewise, in the definition of substituent $R_{16}$, the term "pyridyl" includes 2-, 3- or 4-pyridyl.

Preferred compounds of formula (I) include those wherein $R_2$ is a group of the formula (Ia) wherein $R_3$ and $R_5$ are cis as follows:

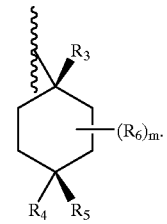

Other preferred compounds of formula (I) include those wherein $R_2$ is a group of the formula (Ia) wherein the dashed line represents a single bond and $R_3$ and $R_4$ are cis.

Other preferred compounds of formula (I) include those wherein R is cyclohexyl, cyclopentyl, methylenecyclopropyl, isopropyl, phenyl or 4-fluoro-phenyl.

Other preferred compounds of formula (I) include those wherein $R_1$ is $C_1$–$C_2$ alkyl optionally substituted by up to three fluorine atoms, and, more preferably, those wherein $R_1$ is ethyl.

Other preferred compounds of formula (I) include those wherein $R_2$ is a group of formula (Ia) wherein the dashed bond represents a single bond.

Other preferred compounds of formula (I) include those wherein $R_2$ is a group of formula (Ia) wherein the dashed line represents a single bond and $R_3$ is cyano.

Other preferred compounds of formula (I) include those wherein $R_2$ is a group of formula (Ia) wherein the dashed line represents a single bond, m is 0 and $R_5$ is hydrogen.

Other preferred compounds of formula (I) include those wherein $R_2$ is a group of formula (Ia) wherein the dashed line represents a single bond and $R_4$ is carboxy, —$CH_2OH$, or —$CH_2C(O)NH_2$.

Preferred individual compounds of formula (I) include: 1-(1-cyclopentyl-3-ethyl-1H-indazol-6-yl)-4-oxo-cyclohexanecarbonitrile; trans-4-cyano-4-(1-cyclopentyl-3-ethyl-1H-indazol-6-yl)-cyclohexanecarboxylic acid methyl ester; cis-4-cyano-4-(1-cyclopentyl-3-ethyl-1H-indazol-6-yl)-cyclohexanecarboxylic acid methyl ester; 1-(1-cyclohexyl-3-ethyl-1H-indazol-6-yl)-4-oxo-cyclohexanecarbonitrile; cis-4-cyano-4-(1-cyclohexyl-3-ethyl-1H-indazol-6-yl)-cyclohexanecarboxylic acid methyl ester; trans-4-cyano-4-(1-cyclohexyl-3-ethyl-1H-indazol-6-yl)-cyclohexanecarboxylic acid methyl ester; cis-4-cyano-4-(1-cyclohexyl-3-ethyl-1H-indazol-6-yl)-cyclohexanecarboxylic acid; trans-4-cyano-4-(1-cyclohexyl-3-ethyl-1H-indazol-6-yl)-cyclohexanecarboxylic acid; 1-(cyclohexyl-3-ethyl-1H-indazol-6yl)-cis-4-hydroxylmethylcyclohexane carbonitrile; cis-4-cyano-4-(1-cyclohexyl-3-ethyl-1H-indazol-6-yl)-cyclohexanecarboxylic acid amide and trans-4-cyano-4-(1-cyclohexyl-3-ethyl-1H-indazol-6-yl)-cyclohexanecarboxylic acid amide.

The phrase "pharmaceutically acceptable salt(s)," as used herein, unless otherwise indicated, includes salts of acidic or basic groups which may be present in the compounds suitable for use in the present invention, e.g., the compounds of formula (I) herein. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts.

Certain compounds suitable for use in the present invention such as, for example, certain compounds of formula (I), may have asymmetric centers and therefore exist in different enantiomeric forms. All optical isomers and stereoisomers of such compounds, and mixtures thereof, are considered to be within the scope of the invention. With respect to such compounds, the present invention includes the use of a racemate, a single enantiomeric form, a single diastereomeric form, or mixtures thereof. Moreover, such compounds may also exist as tautomers. Accordingly, the present invention relates to the use of all such tautomers and mixtures thereof.

The present invention further relates to pharmaceutical compositions for the treatment of CHF in a mammal, comprising a CHF treating amount of a compound which inhibits PDE type IV and the production of TNF. As discussed earlier with respect to the novel methods of the present invention, suitable compounds for use in such pharmaceutical compositions include the substituted indazole derivatives disclosed in the aforementioned commonly-assigned PCT published application WO 97/42174, including, for example, the compounds of formula (I) herein, or a pharmaceutically acceptable salt thereof, together with a pharmaceutically acceptable vehicle, diluent or carrier.

DETAILED DESCRIPTION OF THE INVENTION

The preparation of the compounds suitable for use in the present invention including the compounds of formula (I) herein, and the preferred compounds thereof, can be carried out by one skilled in the art in any suitable manner, e.g., according to one or more of the synthetic methods outlined in the synthetic schemes and examples described in considerable detail in the aforementioned PCT published application WO 97/42174.

For administration to humans in the prophylactic, palliative or curatve treatment of CHF, oral dosages of, e.g., a compound of formula (I), or a pharmaceutically acceptable salt thereof (the active compounds), are generally in the range of from about 0.1 mg to about 1000 mg per day for an average adult patient (about 70 kg). Individual tablets or capsules should generally contain from about 0.1 mg to about 1000 mg of active compound, in a suitable pharmaceutically acceptable vehicle, diluent or carrier. Dosages for intravenous administration are typically within the range of from about 0.1 mg to about 500 mg per single dose as required. For intranasal or inhaler administration, the dosage is generally formulated as from about a 0.1% to about a 1% (w/v) solution. In practice, the physician will determine the actual dosage which will be most suitable for an individual patient and it will vary with age, weight and response of the particular patient. The above dosages are exemplary of the average case but there can, of course, be individual instances where higher or lower dosage ranges are merited, and all such dosages are within the scope of the present invention.

For human use, the active compounds of the present invention can be administered alone, but will generally be administered in an admixture with a pharmaceutically acceptable vehicle, diluent or carrier selected with regard to the intended route of administration and standard pharmaceutical practice. For example, they may be administered orally in the form of tablets comprising such excipients as starch or lactose, or in capsules either alone or in admixture with excipients, or in the form of elixirs or suspensions comprising flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

Additionally, the active compounds may be administered topically and this may be done by way of creams, jellies, gels, pastes, and ointments, in accordance with standard pharmaceutical practice.

The active compounds may also be administered to a mammal other than a human such as, for example, a companion animal. The dosage to be administered will depend, for example, on the species and the disease or disorder being treated. The active compounds may be administered in the form of a capsule, bolus, tablet or liquid drench. The active compounds may also be administered by injection or as an implant. Such formulations are prepared in a conventional manner in accordance with standard veterinary practice. As an alternative, the compounds of the present invention may be administered with the feed stuff and for this purpose a concentrated feed additive or premix may be prepared for mixing with the normal feed.

It is to be understood that the methods and pharmaceutical compositions of the present invention may further include, or be administered to patients already taking, other compounds, e.g., cardiac glycosides, vasodilators, β-adrenergic blockers, calcium channel antagonists, and the like.

Assay for the Inhibition of PDE IV

The ability of the compounds comprising the methods and pharmaceutical compositions of the present invention, as exemplified by formula (I), or the pharmaceutically acceptable salts thereof, to inhibit PDE IV may be determined using a suitable method such as, for example, the assay described immediately below.

Human lung tissue (from about 30 to about 40 grams (g)) is placed in a suitable buffer (about 50 milliliters (mL) of Tris/phenylmethylsulfonyl fluoride (PMSF)/sucrose buffer at about pH 7.4) and homogenized using a Tekmar Tissumizer® (Tekmar® Co., 7143 Kemper Road, Cincinnati, Ohio 45249) at full speed for about 30 seconds (sec). The homogenate is centrifuged (at about 48,000×g, for about 70 minutes (min.), at about 4° C.) and the supernatant is filtered twice (through a 0.22 μm filter) and applied to a Mono FPLC column (Pharmacia® LKB Biotechnology, 800 Centennial Avenue, Piscataway, N.J. 08854) pre-equilibrated with buffer (Tris/PMSF of about pH 7.4). A flow rate of about 1 mL per min. is used to apply the sample to the column, followed by a 2 mL per min. flow rate for subsequent washing and elution. Sample is eluted using an increasing, stepwise NaCl gradient in buffer (Tris/PMSF of about pH 7.4) and 8 mL fractions are collected and assayed for specific PDE IV activity determined by [$^6$H]cAMP hydrolysis and the ability of a known PDE IV inhibitor such as, for example, rolipram, to inhibit that [$^3$H]cAMP hydrolysis. Appropriate fractions are pooled, diluted with ethylene glycol (about 2 mL of ethylene glycol per about 5 mL of enzyme prep.) and stored at about −20° C. until use.

Compounds are dissolved in DMSO at a concentration of about 10 mM and diluted in water (1:25, about 400 μM of the compound in about 4% DMSO). Further serial dilutions are made in about 4% DMSO to achieve the desired concentrations. The final DMSO concentration in the assay tube is about 1%. In duplicate, the following are added, in order, to a 12×75 mm glass tube (all concentrations are given as final concentrations in the assay tube).

i) 25 microliter (μL) of compound or DMSO (about 1%, for control and blank).
ii) 25 μl of Tris buffer of about pH 7.5.
iii) [$^3$H]cAMP (about 1 μM).
iv) 25 μl of PDE IV enzyme (for blank, enzyme is preincubated in boiling water for about 5 min).

The reaction tubes are shaken and placed in a water bath (at about 37° C.) for about 20 min., at which time the reaction is stopped by placing the tubes in a boiling water bath for about 4 min. Washing buffer (about 0.5 mL of about 0.1M 4-(2-hydroxyethyl)-1-piperazine ethanesulfonic acid (HEPES)/about 0.1M NaCl, at about pH 8.5) is added to each reaction tube on an ice bath. The contents of each reaction tube are applied to an AFF-Gel 601 column (borate affinity gel, about 1 mL bed volume, Biorad Laboratories, P.O. Box 1229, 85A Marcus Drive, Melville, N.Y. 11747) previously equilibrated with washing buffer. [$^6$H]cAMP is washed with 2×6 mL of washing buffer, and [$^6$H]5'AMP is then eluted with about 4 mL of about 0.25M acetic acid. After vortexing, about 1 mL of the elution is added to about 3 mL of scintillation fluid in a suitable vial, vortexed and counted (counts per min or "cpm") for [$^3$H].

$$\% \text{ inhibition} = 1 - \frac{\text{average cpm (test compound)} - \text{average cpm (blank)}}{\text{average cpm (control)} - \text{average cpm (blank)}}$$

IC$_{50}$ is defined as that concentration of compound which inhibits about 50% of specific hydrolysis of [$^3$H]cAMP to [$^8$H]5'AMP. Preferred compounds of the invention are those providing an IC$_{50}$ of less than about 100 μm. Particularly preferred compounds of the invention are those providing an IC$_{50}$ of less than about 30 μm.

Assay for the Inhibition of TNF Production

The ability of the compounds of the methods and pharmaceutical compositions of the present invention, as exemplified by formula (I), or the pharmaceutically acceptable salts thereof, to inhibit TNF production and, consequently, demonstrate their effectiveness for treating disease involving the production of TNF may be determined using a suitable method such as, for example, the in vitro assay described immediately below.

Peripheral blood (about 100 mL) from human volunteers is collected in ethylenediaminetetraacetic acid (EDTA). Mononuclear cells are isolated by FICOLL/Hypaque and washed three times in incomplete HBSS, resuspended in a final concentration of about 1×10$^6$ cells per mL in pre-warmed RPMI (containing about 5% FCS, glutamine, pen/strep and nystatin) and the monocytes are plated at about 1×10$^6$ cells in about 0.1 mL in 24-well plates. The cells are incubated at about 37° C. (about 5% carbon dioxide) and allowed to adhere to plates for about 2 hours, after which time, the non-adherent cells are removed by gentle washing. Test compounds (about 10 μl) are then added to the cells at between 3 to 4 concentrations each and incubated for about 1 hour. LPS (about 10 μl) is added to appropriate wells. Plates are incubated overnight (about 18 hours) at about 37° C. At the end of the incubation period, TNF was analyzed by a sandwich ELISA (R&D Quantikine Kit). IC$_{50}$ determinations are made for each compound. Preferred compounds of the invention are those providing an IC$_{50}$ of less than about 100 μm. Particularly preferred compounds of the invention are those providing an IC$_{50}$ of less than about 30 μm.

What is claimed is:

1. A method for treating congestive heart failure in a mammal, comprising administering to said mammal a congestive heart failure treating amount of a compound which inhibits phosphodiesterase type IV and the production of tumor necrosis factor.

2. The method as defined in claim 1 wherein said compound is of the formula

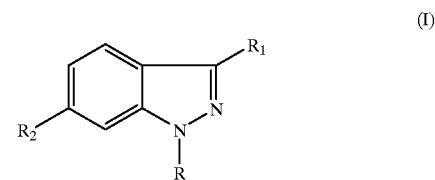

(I)

and the pharmaceutically acceptable salts thereof, wherein:

R is hydrogen, C$_1$–C$_6$ alkyl, —(CH$_2$)$_n$(C$_3$–C$_7$ cycloalkyl) wherein n is 0 to 2, (C$_1$–C$_6$ alkoxy)C$_1$–C$_6$ alkyl, C$_2$–C$_6$ alkenyl, —(CH$_2$)$_n$(C$_3$–C$_9$ heterocyclyl) wherein n is 0 to 2, or —(Z')$_b$(Z")$_c$(C$_6$–C$_{10}$ aryl) wherein b and c are independently 0 or 1, Z' is C$_1$–C$_6$ alkylene or C$_2$–C$_6$ alkenylene, and Z" is O, S, SO$_2$, or NR$_9$, and wherein said alkyl, alkenyl, alkoxyalkyl, heterocyclyl, and aryl moieties of said R groups are optionally substituted by 1 to 3 substituents independently selected from halo, hydroxy, C$_1$–C$_5$ alkyl, C$_2$–C$_5$ alkenyl, C$_1$–C$_5$ alkoxy, C$_3$–C$_6$ cycloalkoxy, trifluoromethyl, nitro, CO$_2$R$_9$, C(O)NR$_9$R$_{10}$, NR$_9$NR$_{10}$ and SO$_2$NR$_9$R$_{10}$;

R$_1$ is hydrogen, C$_1$–C$_7$ alkyl, C$_2$–C$_3$ alkenyl, phenyl, C$_3$–C$_7$ cycloalkyl, or (C$_3$–C$_7$ cycloalkyl)C$_1$–C$_2$ alkyl, wherein said alkyl, alkenyl and phenyl R$_1$ groups are optionally substituted by 1 to 3 substituents independently selected from the group consisting of methyl, ethyl, trifluoromethyl, and halo;

$R_2$ is selected from the group consisting of

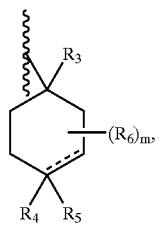
(Ia)

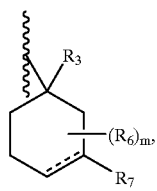
(Ib)

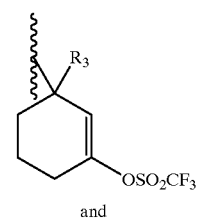
(Ic)

and

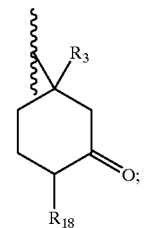
(Id)

wherein the dashed line in formulae (Ia) and (Ib) represents a single or a double bond;

m is 0 to 4;

$R_3$ is hydrogen, halo, cyano, $C_1$–$C_4$ alkyl optionally substituted by 1 to 3 halo groups, $CH_2NHC(O)C(O)NH_2$, cyclopropyl optionally substituted by $R_{11}$, $R_{17}$, $CH_2OR_9$, $NR_9R_{10}$, $CH_2NR_9R_{10}$, $CO_2R_9$, $C(O)NR_9R_{10}$, $C\equiv CR_{11}$, $C(Z)H$ or $CH=CR_{11}R_{11}$;

$R_4$ is hydrogen, $C(Y)R_{14}$, $CO_2R_{14}$, $C(Y)NR_{17}R_{14}$, CN, $C(NR_{17})NR_{17}R_{14}$, $C(NOR_9)R_{14}$, $C(O)NR_9NR_9C(O)R_9$, $C(O)NR_9NR_{17}R_{14}$, $C(NOR_{14})R_9$, $C(NR_9)NR_{17}R_{14}$, $C(NR_{14})NR_9R_{10}$, $C(NCN)NR_{17}R_{14}$, $C(NCN)S(C_1–C_4$ alkyl), $CR_9R_{10}OR_{14}$, $CR_9R_{10}SR_{14}$, $CR_9R_{10}S(O)_nR_{15}$ wherein n is 0 to 2, $CR_9R_{10}NR_{14}R_{17}$, $CR_9R_{10}NR_{17}SO_2R_{15}$, $CR_9R_{10}NR_{17}C(Y)R_{14}$, $CR_{R10}NR_{17}CO_2R_{15}$, $CR_9R_{10}NR_{17}C(Y)NR_{17}R_{14}$, $CR_9R_{10}NR_{17}C(NCN)NR_{17}R_{14}$, $CR_9R_{10}NR_{17}C(CR_9NO_2)S(C_1–C_4$ alkyl), $CR_9R_{10}CO_2R_{15}$, $CR_9R_{10}C(Y)NR_{17}R_{14}$, $CR_9R_{10}C(NR_{17})NR_{17}R_{14}$, $CR_9R_{10}CN$, $CR_9R_{10}C(NOR_{10})R_{14}$, $CR_9R_{10}NR_{17}C(NR_{17})S(C_1–C_4$ alkyl), $CR_9R_{10}NR_{17}C(NR_{17})NR_{17}R_{14}$, $CR_9R_{10}NR_{17}C(O)C(O)NR_{17}R_{14}$, $CR_9R_{10}NR_{17}C(O)C(O)OR_{14}$, tetrazolyl, thiazolyl, imidazolyl, imidazolidinyl, pyrazolyl, thiazolidinyl, oxazolyl, oxazolidinyl, triazolyl, isoxazolyl, oxadiazolyl, thiadiazolyl, $CR_9R_{10}$(tetrazolyl), $CR_9R_{10}$(thiazolyl), $CR_9R_{10}$(imidazolyl), $CR_9R_{10}$(imidazolidinyl), $CR_9R_{10}$(pyrazolyl), $CR_9R_{10}$(thiazolidinyl), $CR_9R_{10}$(oxazolyl), $CR_9R_{10}$(oxazolidinyl), $CR_9R_{10}$(triazolyl), $CR_9R_{10}$(isoxazolyl), $CR_9R_{10}$(oxadiazolyl), $CR_9R_{10}$(thiadiazolyl), $CR_9R_{10}$(morpholinyl), $CR_9R_{10}$(piperidinyl), $CR_9R_{10}$(piperazinyl), or $CR_9R_{10}$(pyrrolyl), wherein said heterocyclic groups and moieties for said $R_4$ substituents are optionally substituted by 1 to 3 $R_{14}$ substituents;

$R_5$ is $R_9$, $OR_9$, $CH_2OR_9$, cyano, $C(O)R_9$, $CO_2R_9$, $C(O)NR_9R_{10}$, or $NR_9R_{10}$, provided that $R_5$ is absent when the dashed line in formula (Ia) represents a double bond;

or $R_4$ and $R_5$ are taken together to form =O, or $R_8$;

or $R_5$ is hydrogen and $R_4$ is $OR_{14}$, $SR_{14}$, $S(O)_nR_{15}$ wherein n is 0 or 2, $SO_2NR_{17}R_{14}$, $NR_{17}R_{14}$, $NR_{14}C(O)R_9$, $NR_{17}C(Y)R_{14}$, $NR_{17}C(O)OR_{15}$, $NR_{17}C(Y)NR_{17}R_{14}$, $NR_{17}SO_2NR_{17}R_{14}$, $NR_{17}C(NCN)NR_{17}R_{14}$, $NR_{17}SO_2R_{15}$, $NR_{17}C(CR_9NO_2)NR_{17}R_{14}$, $NR_{17}C(NCN)S(C_1–C_4$ alkyl), $NR_{17}C(CR_9NO_2)S(C_1–C_4$ alkyl), $NR_{17}C(NR_{17})NR_{17}R_{14}$, $NR_{17}C(O)C(O)NR_{17}R_{14}$, or $NR_{17}C(O)C(O)OR_{14}$;

each $R_6$ is independently selected from methyl and ethyl optionally substituted by 1 to 3 halo groups;

$R_7$ is $OR_{14}$, $SR_{14}$, $SO_2NR_{17}R_{14}$, $NR_{17}R_{14}$, $NR_{14}C(O)R_9$, $NR_{17}C(Y)R_{14}$, $NR_{17}C(O)OR_{15}$, $S(O)_nR_{12}$ wherein n is 0 to 2, $OS(O)_2R_{12}$, $OR_{12}$, $OC(O)NR_{13}R_{12}$, $OC(O)R_{13}$, $OCO_2R_{13}$, $O(CR_{12}R_{13})_mOR_{12}$ wherein m is 0 to 2, $CR_9R_{10}$ $OR_{14}$, $CR_9R_{10}NR_{17}R_{14}$, $C(Y)R_{14}$, $CO_2R_{14}$, $C(Y)NR_{17}R_{14}$, CN, $C(NR_{17})NR_{17}R_{14}$, $C(NOR_9)R_{14}$, $C(O)NR_9NR_9C(O)R_9$, $C(O)NR_9NR_{17}R_{14}$, $C(NOR_{14})R_9$, $C(NR_9)NR_{17}R_{14}$, $C(NR_{14})NR_9R_{10}$, $C(NCN)NR_{17}R_{14}$, $C(NCN)S(C_1–C_4$ alkyl), tetrazolyl, thiazolyl, imidazolyl, imidazolidinyl, pyrazolyl, thiazolidinyl, oxazolyl, oxazolidinyl, triazolyl, isoxazolyl, oxadiazolyl, or thiadiazolyl, wherein said $R_7$ heterocyclic groups are optionally substituted by 1 to 3 $R_{14}$ substituents;

$R_8$ is =$NR_{15}$, =$NCR_9R_{10}(C_2–C_6$ alkenyl), =$NOR_{14}$, =$NOR_{19}$, =$NOCR_9R_{10}(C_2–C_6$ alkenyl), =$NNR_9R_{14}$, =$NNR_9R_{19}$, =NCN, =$NNR_9C(Y)NR_9R_{14}$, =$C(CN)_2$, =$CR_{14}CN$, =$CR_{14}CO_2R_9$, =$CR_{14}C(O)NR_9R_{14}$, =$C(CN)NO_2$, =$C(CN)CO_2(C_1–C_4$ alkyl), =$C(CN)OCO_2(C_1–C_4$ alkyl), =$C(CN)(C_1–C_4$ alkyl), =$C(CN)C(O)NR_9R_{14}$, 2-(1,3-dithiane), 2-(1,3-dithiolane), dimethylthio ketal, diethylthio ketal, 2-(1,3-dioxolane), 2-(1,3-dioxane), 2-(1,3-oxathiolane), dimethyl ketal or diethyl ketal;

each $R_9$ and $R_{10}$ is independently hydrogen or $C_1$–$C_4$ alkyl optionally substituted by up to three fluorine atoms;

each $R_{11}$ is independently fluoro or $R_{10}$;

each $R_{12}$ is independently $C_1$–$C_6$ alkyl, $C_2$–$C_3$ alkenyl, $C_3$–$C_7$ cycloalkyl, $(C_3$–$C_7$ cycloalkyl)$C_1$–$C_2$ alkyl, $C_6$–$C_{10}$ aryl, or $C_3$–$C_9$ heterocyclyl, wherein said $R_{12}$ groups are optionally substituted by 1 to 3 substituents independently selected from the group consisting of methyl, ethyl, trifluoromethyl, and halo;

each $R_{13}$ is independently hydrogen or $R_{12}$;

each $R_{14}$ is independently hydrogen or $R_{15}$, or when $R_{14}$ and $R_{17}$ are as $NR_{17}R_{14}$ then $R_{17}$ and $R_{14}$ can be taken together with the nitrogen to form a 5 to 7 membered ring optionally containing at least one additional heteroatom selected from O, N and S;

each $R_{15}$ is independently $C_1$–$C_6$ alkyl or —$(CR_9R_{10})_nR_{16}$ wherein n is 0 to 2 and $R_{16}$ and said $C_1$–$C_6$ alkyl are optionally substituted by 1 to 3 substituents independently selected from halo, nitro, cyano, $NR_{10}R_{17}$, $C(O)R_9$, $OR_9$, $C(O)NR_{10}R_{17}$, $OC(O)NR_{10}R_{17}$, $NR_{17}C(O)NR_{17}R_{10}$, $NR_{17}C(O)R_{10}$, $NR_{17}C(O)O(C_1$–$C_4$ alkyl), $C(NR_{17})NR_{17}R_{10}$, $C(NCN)NR_{17}R_{10}$, $C(NCN)S(C_1$–$C_4$ alkyl), $NR_{17}C(NCN)S(C_1$–$C_4$ alkyl), $NR_{17}C(NCN)NR_{17}R_{10}$, $NR_{17}SO_2(C_1$–$C_4$ alkyl), $S(O)_n(C_1$–$C_4$ alkyl) wherein n is 0 to 2, $NR_{17}C(O)C(O)NR_{17}R_{10}$, $NR_{17}C(O)C(O)R_{17}$, thiazolyl, imidazolyl, oxazolyl, pyrazolyl, triazolyl, tetrazolyl, and $C_1$–$C_2$ alkyl optionally substituted with one to three fluorine atoms;

each $R_{16}$ is independently $C_3$–$C_7$ cycloalkyl, pyridyl, pyrimidyl, pyrazolyl, imidazolyl, triazolyl, pyrrolyl, piperazinyl, piperidinyl, morpholinyl, furanyl, thienyl, thiazolyl, quinolinyl, naphthyl, or phenyl;

each $R_{17}$ is independently $OR_9$ or $R_{10}$;

$R_{18}$ is H, $C(Y)R_{14}$, $CO_2R_4$, $C(Y)NR_{17}R_{14}$, CN, $C(NR_{17})NR_{17}R_{14}$, $C(NOR_9)R_{14}$, $C(O)NR_9NR_9C(O)R_9$, $C(O)NR_9NR_{17}R_{14}$, $C(NOR_{14})R_9$, $C(NR_9)NR_{17}R_{14}$, $C(NR_{14})NR_9R_{10}$, $C(NCN)NR_{17}R_{14}$, $C(NCN)S(C_1$–$C_4$ alkyl), $CR_9R_{10}OR_{14}$, $CR_9R_{10}SR_{14}$, $CR_9R_{10}S(O)_nR_{15}$ wherein n is 0 to 2, $CR_9R_{10}NR_{14}R_{17}$, $CR_9R_{10}NR_{17}SO_2R_{15}$, $CR_9R_{10}NR_{17}C(Y)R_{14}$, $CR_9R_{10}NR_{17}CO_2R_{15}$, $CR_9R_{10}NR_{17}C(Y)NR_{17}R_{14}$, $CR_9R_{10}NR_{17}C(NCN)NR_{17}R_{14}$, $CR_9R_{10}NR_{17}C(CR_9NO_2)S(C_1$–$C_4$ alkyl), tetrazolyl, thiazolyl, imidazolyl, imidazolidinyl, pyrazolyl, thiazolidinyl, oxazolyl, oxazolidinyl, triazolyl, isoxazolyl, oxadiazolyl, thiadiazolyl, wherein said heterocyclic groups are optionally substituted by 1 to 3 $R_{14}$ substituents;

$R_{19}$ is —$C(O)R_{14}$, —$C(O)NR_9R_{14}$, —$S(O)_2R_{15}$, or —$S(O)_2NR_9R_{14}$;

each Y is independently =O or =S; and

Z is =O, =$NR_{17}$, =NCN, =$C(CN)_2$, =$CR_9CN$, =$CR_9NO_2$, =$CR_9CO_2R_9$, =$CR_9C(O)NR_9R_{10}$, =$C(CN)CO_2(C_1$–$C_4$ alkyl) or =$C(CN)C(O)NR_9R_{10}$.

3. The method as defined in claim 2 wherein R of said compound is cyclohexyl, cyclopentyl, methylenecyclopropyl, isopropyl, phenyl or 4-fluorophenyl.

4. The method as defined in claim 3 wherein $R_1$ is $C_1$–$C_2$ alkyl optionally substituted by up to three fluorine atoms.

5. The method as defined in claim 4 wherein $R_1$ is ethyl.

6. The method as defined in claim 4 wherein $R_2$ is a group of formula (Ia) wherein the dashed line represents a single bond.

7. The method as defined in claim 6 wherein $R_3$ is cyano.

8. The method as defined in claim 7 wherein m is 0 and $R_5$ is hydrogen.

9. The method as defined in claim 7 wherein $R_4$ is carboxy, —$CH_2OH$ or —$CH_2C(O)NH_2$.

10. The method as defined in claim 2 wherein $R_2$ of said compound is a group of formula (Ia) wherein $R_3$ and $R_5$ are cis as follows:

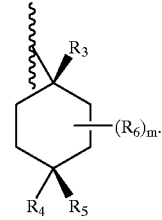

11. The method as defined in claim 2 wherein said compound is selected from the group consisting of:

1-(1-cyclopentyl-3-ethyl-1H-indazol-6-yl)4-oxo-cyclohexanecarbonitrile;

trans4-cyano4-(1-cyclopentyl-3-ethyl-1H-indazol-6-yl)-cyclohexanecarboxylic acid methyl ester;

cis4-cyano4-(1-cyclopentyl-3-ethyl-1H-indazol-6-yl)-cyclohexanecarboxylic acid methyl ester;

1-(1-cyclohexyl-3-ethyl-1H-indazol-6-yl)4-oxo-cyclohexanecarbonitrile;

cis4-cyano4-(1-cyclohexyl-3-ethyl-1H-indazol-6-yl)-cyclohexanecarboxylic acid methyl ester;

trans4-cyano4-(1-cyclohexyl-3-ethyl-1H-indazol-6-yl)-cyclohexanecarboxylic acid methyl ester;

cis4-cyano4-(1-cyclohexyl-3-ethyl-1H-indazol-6-yl)-cyclohexanecarboxylic acid;

trans4-cyano4-(1-cyclohexyl-3-ethyl-1H-indazol-6-yl)-cyclohexanecarboxylic acid;

1-(cyclohexyl-3-ethyl-1H-indazol-6yl)-cis4-hydroxylmethylcyclohexane carbonitrile;

cis4-cyano4-(1-cyclohexyl-3-ethyl-1H-indazol-6-yl)-cyclohexanecarboxylic acid amide and trans4-cyano4-(1-cyclohexyl-3-ethyl-1H-indazol-6-yl)-cyclohexanecarboxylic acid amide.

\* \* \* \* \*